US00PP28612P2

(12) United States Plant Patent
Ui et al.

(10) Patent No.: US PP28,612 P2
(45) Date of Patent: Nov. 7, 2017

(54) ***PETUNIA-CALIBRACHOA* HYBRID PLANT NAMED 'SAKPXC017'**

(50) Latin Name: ***Petunia-Calibrachoa* intergeneric hybrid**
Varietal Denomination: SAKPXC017

(71) Applicant: Sakata Seed Corporation, Tsuzuki-Ku, Yokohama (JP)

(72) Inventors: Akinobu Ui, Iwata (JP); Shin Ishikawa, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,096

(22) Filed: Mar. 30, 2016

(51) Int. Cl.
*A01H 5/02* (2006.01)

(52) U.S. Cl.
USPC ..... Plt./356.11

(58) Field of Classification Search
USPC ..... Plt./356.11
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A new *Petunia-Calibrachoa* hybrid plant particularly distinguished by having light yellow flowers with darker veins and a compact plant habit, is disclosed.

4 Drawing Sheets

Genus and species: *Petunia-Calibrachoa* intergeneric hybrid.

Variety denomination: 'SAKPXC017'.

BACKGROUND OF THE NEW PLANT

The present invention comprises a new and distinct variety of *Petunia-Calibrachoa* (Petchoa) referred to by the variety name 'SAKPXC017'. Variety 'SAKPXC017' originated from a hybridization in Kakegawa, Japan in December 2011. The female parent was a proprietary *Petunia* Hybrida line named 'GY2-1E-6' (unpatented), which had a yellow flower color and a mounding plant habit. The male parent was a proprietary *Calibrachoa Hybrida* line named 'AM9-83A-1B-2A' (unpatented), which had a yellow flower color and a compact plant habit.

In December 2011, the breeder made an initial cross between the female and male breeding lines. In January 2012, 34 ovules were obtained and ovule culture was done to rescue the embryo. In July 2012, 5 plants were obtained after the acclimatization process was completed. Segregation in the $F_1$ generation resulted in plants having yellow, cream and brown flower colors with vein and mounding or semi-mounding habits. The breeder selected a plant from the group of plants that exhibited a yellow flower color that was well blooming and had a mounding plant habit. The line was given the experimental name 'K2013-J-228'.

In August 2012, the selection was vegetatively propagated by cuttings to produce rooted cuttings and plants of the selection were cultivated evaluated in an open field. In November 2012, the breeder observed the selected line to have its distinct characteristics remain stable. In December 2012, the selection was propagated again and plants were cultivated. In April 2013, the breeder confirmed that the distinct characteristics of the selection were fixed and stable. All breeding work was conducted at Kakegawa Research station in Kakegawa Japan. The selection was named 'SAKPXC017'.

SUMMARY

The following are the most outstanding and distinguishing characteristics of this new variety when grown under normal horticultural practices in Salinas, Calif.

1. Light yellow flower color with darker veins; and
2. A mounding plant habit.

DESCRIPTION OF THE PHOTOGRAPHS

This new *Petunia-Calibrachoa* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
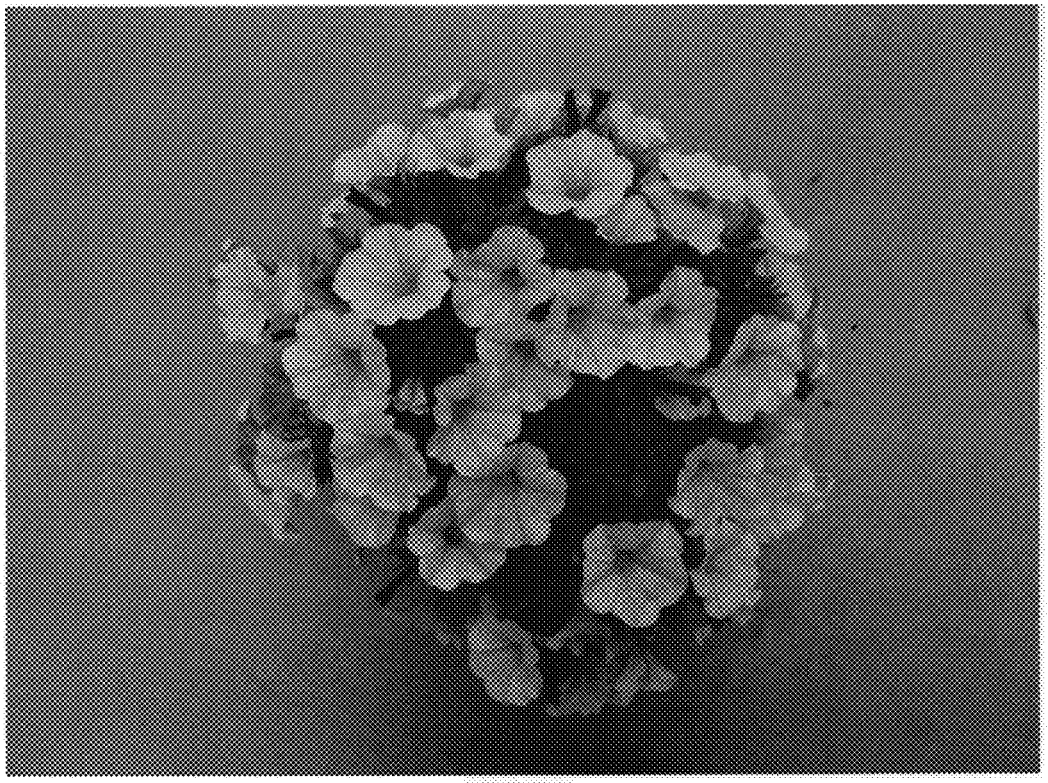
FIG. 1 shows the overall plant habit of a young plant grown in a pot.
Figure 2:
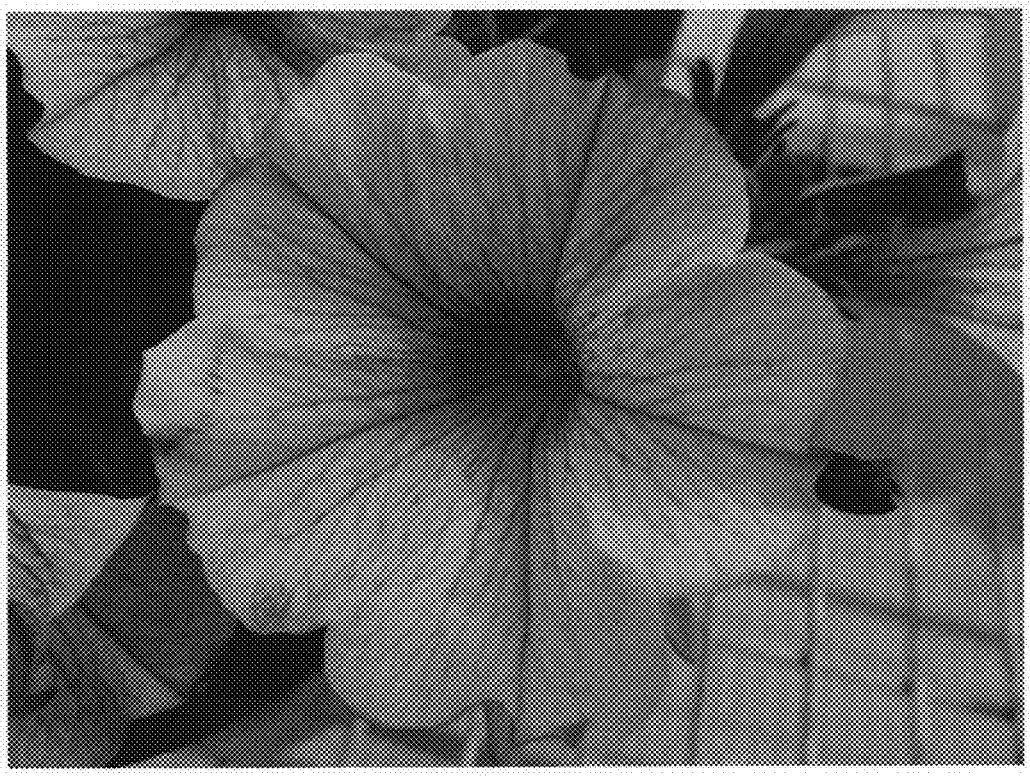
FIG. 2 shows a close-up of the buds, and flower, of the plant shown in FIG. 1.
Figure 3:
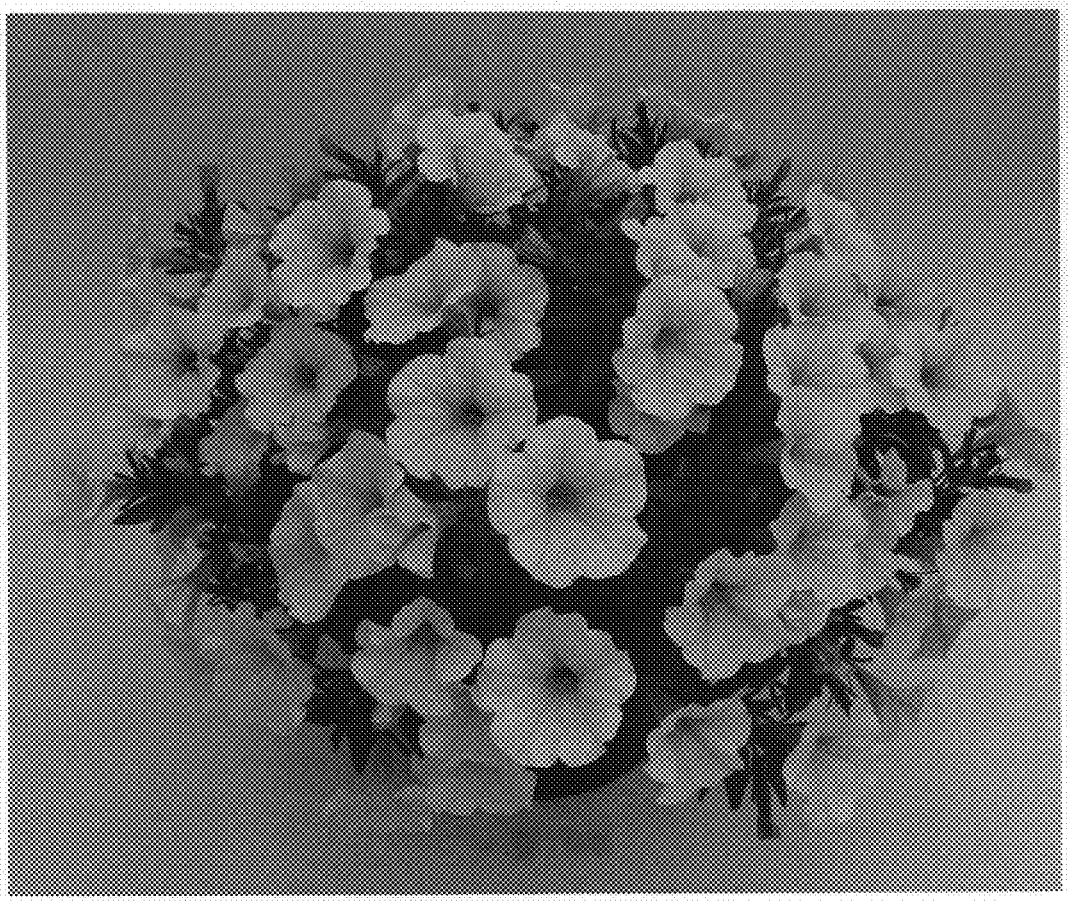
FIG. 3 shows the overall plant habit of a mature plant grown in a pot.
Figure 4:
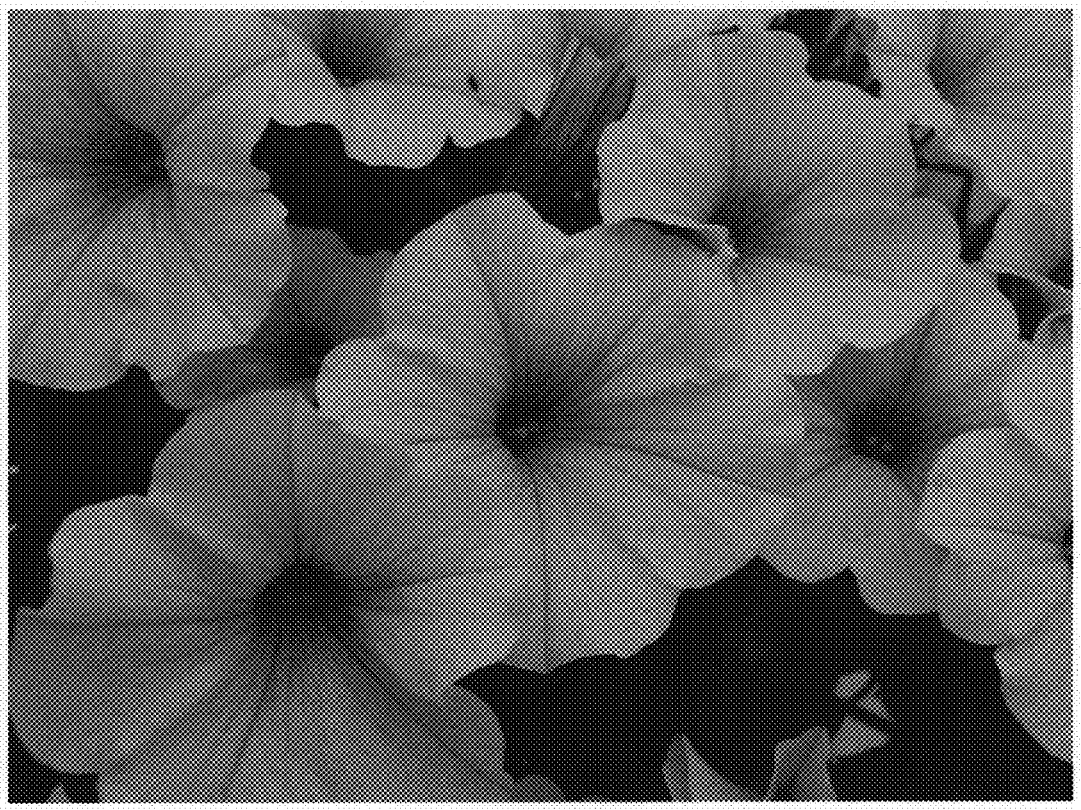
FIG. 4 shows a close-up of the buds and flower of the plant shown in FIG. 3.

The following detailed descriptions set forth the distinctive characteristics of 'SAKPXC017'. Plants were five months from stick date and two and a half months from transplant. Color references are to The R.H.S. Colour Chart of The Royal Horticultural Society of London (R.H.S.), $4^{th}$ edition. Anatomic labels are from *The Cambridge Illustrated Glossary of Botanical Terms*, by M. Hickey and C. King, Cambridge University.

Classification:

*Family*.—Solanaceae.

*Botanical*.—*Petunia-Calibrachoa* hybrid.

*Common*.—Petchoa, *petunia-calibrachoa*.
*Designation*.—'SAKPXC017'.

Parentage:
*Female parent*.—'GY2-1E-6' (unpatented).
*Male parent*.—'AM9-83A-1B-2A' (unpatented).

Growth:
*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water), a root inducing solution, immediately prior to sticking into the cell trays. Cuttings were stuck into plastic cell trays having 98 cells, and containing a moistened peat moss-based growing medium. For the first week, the cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:
*Habit*.—Mounding.
*Life cycle*.—Tender perennial.
*Height*.—18.0 cm from soil line to top of foliage.
*Spread*.—40.0 cm.
*Time and conditions to produce a rooted cutting*.—4 weeks.
*Time to bloom from propagation*.—8 to 10 weeks.

Stems:
*General*.—Dull in appearance and circular in cross-section.
*Stem color*.—RHS 144A (Yellow-Green).
*Anthocyanin color*.—Very slight (only on peduncle), color is RHS N187A (Greyed-Purple).
*Pubescence*.—Heavy.
*Pubescence color*.—RHS N155A (White).
*Stem diameter*.—4.0 mm (main stems/branches), 3.0 mm (secondary branches/stems).
*Stem length* (*length of entire stem from end to end*).—15.0 cm; from soil line to first node: 1.0 cm.
*Internode length*.—1.0 cm.

Leaves:
*Arrangement*.—Alternate.
*Leaf shape*.—Elliptic.
*Leaf tip*.—Obtuse.
*Leaf base*.—Attenuate.
*Leaf margin*.—Entire.
*Leaf surface*.—Dull.
*Leaf length*.—4.0 cm.
*Leaf width*.—0.9 cm.
*Color*.—Upper surface: RHS 137A (Green). Lower surface: RHS 138A (Green).
*Leaf fragrance*.—Absent.
*Leaf surface pubescence*.—Moderate.
*Leaf surface pubescence color*.—RHS N155A (White).
*Petiole*.—Absent.
*Venation pattern*.—Pinnate.

Flowers:
*Total number of flowers*.—Approximately 110.
*Flowering habit*.—Indeterminate.
*Flower type*.—Solitary.
*Flowering requirements*.—Will flower so long as day length is greater than 12 hours and temperature exceeds 13° C.
*Duration of flower life*.—5 days.
*Shape*.—The flowers are funnel shaped with five fissures and a shallow, yet prominent, indentation of the petal tip at the midvein.
*Flower diameter*.—5.0 cm.
*Flower depth*.—1.0 cm.

Flower buds:
*Shape*.—Ovate.
*Bud surface texture*.—Pubescent.
*Bud length*.—3.5 cm.
*Bud diameter*.—0.8 cm.
*Bud color*.—RHS 1D (Yellow) with RHS 144B (Yellow-Green) and RHS N77A (Purple) veins.

Peduncle:
*Peduncle length*.—1.5 cm.
*Peduncle diameter*.—1.0 mm.
*Peduncle color*.—RHS 144A (Yellow-Green) with very slight anthocyanin on some, anthocyanin color is RHS N187A (Greyed-Purple).
*Peduncle texture*.—Dull, heavy pubescence, pubescence color is RHS N155A (White).

Calyx:
*Arrangement*.—Composed of 5 sepals, fused below the middle.
*Sepal shape*.—Elliptical.
*Sepal apex*.—Obtuse.
*Sepal margin*.—Entire.
*Sepal length*.—2.0 cm.
*Sepal diameter*.—0.4 mm.
*Sepal color*.—Upper surface: RHS 138A (Green). Lower surface: RHS 138A (Green).

Corolla:
*Arrangement*.—Composed of 5 petals, fused.
*Petal pubescence*.—Glabrous.
*Petal shape*.—Bilabiate, fused, margin cleaved.
*Petal length*.—2.5 cm.
*Petal width*.—2.5 cm.
*Petal apex*.—Truncate.
*Petal margin*.—Entire.
*Petal color*.—Lobes: Upper surface: Closest to RHS 11D (Yellow) with RHS 1A (Green-Yellow) veins and RHS 12B (Yellow) eye. Lower surface: RHS 11D (Yellow) with RHS 144B (Yellow-Green) midveins. Corolla tube: Inner surface: Closest to RHS 12B (Yellow) with RHS N77A (Purple) veins. Outer surface: RHS 1D (Yellow) with RHS 144B (Yellow-Green) and RHS N77A (Purple) veins.
*Flower tube length*.—2.5 cm.
*Flower tube diameter*.—1.0 cm.
*Flower tube pubescence*.—Inner: Absent. Outer: Moderate.

Reproductive organs:
*Ovary*.—Superior.
*Placenta arrangement*.—Central.
*Pistil number*.—1 (per inflorescence).
*Pistil length*.—1.5 cm.
*Stigma color*.—RHS 143C (Green).
*Style length*.—1.8 cm.
*Style color*.—RHS 154D (Yellow-Green).
*Stamen number*.—5, free.
*Stamen length*.—2.0 cm.
*Stamens color*.—RHS 154D (Yellow-Green).

*Filament color*.—RHS 1D (Yellow).

*Pollen color*.—RHS 11B (Yellow).

*Fragrance*.—Absent.

Seed production: None observed.

Environmental conditions, disease and insect resistance: Excellent resistance to rain, heat and drought. Will not tolerate temperatures below 10° C. Plants are susceptible to *Botrytis*, powdery mildew, various stem and root rots, and certain viruses, like Tobacco Mosaic Virus and Impatiens Necrotic Spotted Virus. Plants can be infested with aphids, leafminer, whitefly and various *Lepitopdera*.

COMPARISON WITH PARENTAL LINES AND KNOWN VARIETY

'SAKPXC017' is a new and unique variety of intergeneric *Calibrachoa-Petunia* owing to its yellow flower color and mounding plant growth habit. 'SAKPXC017' is distinguished from its parents as shown below in Table 1.

TABLE 1

Comparison with Parental Lines

| Characteristic | 'SAKPXC017' | Female Parent 'GY2-1E-6' | Male Parent 'AM9-83A-1B-2A' |
|---|---|---|---|
| Flower color | Yellow | Darker yellow than 'SAICPXC017' | Yellow |
| Plant growth habit | Mounding | Less mounding than 'SAKPXC017' | Compact |

'SAKPXC017' is most similar to the commercial *Calibrachoa-Petunia* variety 'SAKPXC014' (U.S. Plant Pat. No. 19,130), commercially known as SUPERCAL 'Salmon Glow'; however there are differences in the flower color as described in the table below (color references are to The Royal Horticultural Society Colour Chart, 4th edition):

TABLE 2

Comparison with Similar Variety

| Characteristic | 'SAKPXC017' | 'SAKPXC014' |
|---|---|---|
| Petal color, upper surface | Closest to RHS 11D (Yellow) with RHS 1A (Green-Yellow) veins and RHS 12B (Yellow) eye | RHS N78C (Purple) and RHS 69C (Red-Purple) with RHS N163 (Greyed-Orange) veins |
| Petal color, lower surface | RHS 11D (Yellow) with RHS 144B (Yellow-Green) midveins | RHS 69C (Red-Purple) with RHS 151C (Yellow-Green) veins |
| Plant growth habit | Mounding | Spreading |

We claim:

1. A new and distinct cultivar of *Petunia-Calibrachoa* hybrid plant as illustrated and described herein.

* * * * *